US011403778B2

(12) United States Patent
Ciofolo-Veit et al.

(10) Patent No.: US 11,403,778 B2
(45) Date of Patent: Aug. 2, 2022

(54) FETAL DEVELOPMENT MONITORING

(71) Applicant: KONINKLIJKE PHILIPS N.V., Eindhoven (NL)

(72) Inventors: Cybèle Ciofolo-Veit, Meudon (FR); Laurence Rouet, Paris (FR); Caroline Denise Francoise Raynaud, Paris (FR); David Nigel Roundhill, Woodinville, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 346 days.

(21) Appl. No.: 16/612,526

(22) PCT Filed: May 3, 2018

(86) PCT No.: PCT/EP2018/061282
§ 371 (c)(1),
(2) Date: Nov. 11, 2019

(87) PCT Pub. No.: WO2018/206379
PCT Pub. Date: Nov. 15, 2018

(65) Prior Publication Data
US 2020/0202551 A1    Jun. 25, 2020

(30) Foreign Application Priority Data

May 11, 2017 (EP) .................................... 17290061
Sep. 14, 2017 (EP) .................................... 17191021

(51) Int. Cl.
*A61B 6/00* (2006.01)
*G06T 7/70* (2017.01)
(Continued)

(52) U.S. Cl.
CPC .............. *G06T 7/70* (2017.01); *A61B 8/0866* (2013.01); *A61B 8/0883* (2013.01); *A61B 8/463* (2013.01);
(Continued)

(58) Field of Classification Search
IPC ................ A61B 8/0883,8/463, 8/5223, 8/5246, 8/06, 8/488
See application file for complete search history.

(56) References Cited

U.S. PATENT DOCUMENTS 8,882,671 B2   11/2014  Sasaki et al.
2002/0072674 A1  6/2002  Criton et al.
(Continued)

OTHER PUBLICATIONS

International Search Report and Written Opinion for International Application No. PCT/EP2018/061282, filed May 3, 2018, 16 pages.
(Continued)

*Primary Examiner* — Joel F Brutus

(57) ABSTRACT

An ultrasound image processing apparatus (16) is disclosed comprising a processor arrangement (46, 50) adapted to receive a temporal sequence (15) of ultrasound images (150) of at least a chest region (151) of a fetal entity (62) from an ultrasound probe (14), said chest region including the fetal heart (171), said temporal sequence capturing at least part of a cardiac cycle of the fetal heart; identify the chest region of the fetal entity in one or more of the ultrasound images of said temporal sequence; identify a portion of the spine in the identified chest region; calculate an orientation axis (160) of the fetal chest from the identified chest region and the identified spine portion; identify the septum of the fetal heart as a linear structure which is temporally more stable than its surrounding structures in said temporal sequence of ultrasound images and which defines a region of convergence of the movements of the fetal heart during said cardiac cycle; calculate an orientation axis (170) of the fetal heart from the
(Continued)

identified septum; and calculate an angle (θ) between the orientation axis of the fetal chest and the orientation axis of the fetal heart. Also disclosed are an ultrasound imaging system comprising such an ultrasound image processing apparatus, a computer-implemented method of visualizing an orientation of the heart of a fetal entity within said entity and a computer program product for implementing such a method.

11 Claims, 10 Drawing Sheets

(51) Int. Cl.
    *A61B 8/08*     (2006.01)
    *A61B 8/00*     (2006.01)
    *G06T 7/00*     (2017.01)
    *A61B 8/06*     (2006.01)

(52) U.S. Cl.
    CPC .......... *A61B 8/5223* (2013.01); *A61B 8/5246* (2013.01); *G06T 7/0012* (2013.01); *A61B 8/06* (2013.01); *A61B 8/488* (2013.01); *G06T 2207/10016* (2013.01); *G06T 2207/10132* (2013.01); *G06T 2207/30044* (2013.01); *G06T 2207/30048* (2013.01)

(56) References Cited

U.S. PATENT DOCUMENTS

| | | |
|---|---|---|
| 2009/0005679 A1 | 1/2009 | Dala-Krishna |
| 2010/0217123 A1 | 8/2010 | Eran et al. |
| 2014/0296711 A1 | 10/2014 | Lee |
| 2015/0190112 A1* | 7/2015 | Yeo .................. A61B 8/0866 600/443 |

OTHER PUBLICATIONS

Wolter, et al., "Fetal Cardiac Axis in Fetuses with Conotruncal Anomalies", Ultraschall in Med 2017, European Journal of Ultrasound, vol. 38, No. 2, Apr. 4, 2017, pp. 198-205.
Allan, L., "A Practical Approach to Fetal Heart Scanning", Seminars in Perinatology, vol. 24, No. 5, Oct. 1, 2000, pp. 324-330.
Cornstock, C., "Normal Fetal Heart Axis and Position", From the Division of Fetal Imaging, Department of Obstetrics and Gynecology, William Beaumont Hospital, Royal Oak, Michigan, vol. 70, No. 2, Aug. 1, 1987, pp. 255-259.
Sinkovskaya, et al., "Defining the fetal cardiac axis between 11+0 and 14+6 weeks of gestation: experience with 100 consecutive pregnancies", Ultrasound in Obstetrics andGynecology, vol. 36, No. 6, Nov. 24, 2010, pp. 676-681.
Suchet, et al., "Normal Cardiac Axis", Interactive fetal ultrasound & MRI teaching DVD, 2 pages. (Abstract).
Li, et al., "Fetal Lung Segmentation Using Texture-based Boundary Enhancement and Active Contour Models", 2010 3rd International Conference on Biomedical Engineering and Informatics (BMEI 2010), Oct. 1, 2010, pp. 264-268.
European Search Report for European Application No. EP17191021.9.
Crane, et al., "Abnormal fetal cardiac axis in the detection of intrathoracic anomalies and congenital heart disease", Ultrasound Obstet. Gynecol., Aug. 1997;10(2), pp. 90-93.
Salomon, et al., "ISUOG Practice Guidelines: performance of first-trimester fetal ultrasound scan", Ultrasound Obstet Gynecol 2013, 41: pp. 102-113.
Ciofolo et al., "Automatic Myocardium Segmentation in Late-Enhancement MRI", IEEE 5th International Symposium on Biomedical Imaging: From Nano to Macro, May 2008, pp. 225-228.

* cited by examiner

FETAL DEVELOPMENT MONITORING

RELATED APPLICATIONS

This application is the U.S. National Phase application under 35 U.S.C. § 371 of International Application No. PCT/EP2018/061282, filed on May 3, 2018, which claims the benefit of both European Application Serial No. 17290061.5, filed May 11, 2017 and European Application Serial No. 17191021.9, filed Sep. 14, 2017. These applications are hereby incorporated by reference herein.

FIELD OF THE INVENTION

The present invention relates to ultrasound image processing apparatus comprising a processor arrangement adapted to determine the orientation of the fetal heart in a fetal entity (or fetus) from a received temporal sequence of ultrasound images.

The present invention further relates to an ultrasound imaging system including such an ultrasound image processing apparatus.

The present invention further relates to a computer-implemented method of visualizing the orientation of the fetal heart in a fetal entity from a received temporal sequence of ultrasound images.

The present invention further relates to a computer program product for implementing such a computer-implemented method on an ultrasound image processing apparatus.

BACKGROUND OF THE INVENTION

Ultrasonic imaging is routinely used during pregnancy to assess the development of a fetal entity in the mother's womb, for example to detect structural anomalies in the fetus. The traditional way for a clinician to acquire an image of each required view of the prenatal entity is to manipulate an ultrasound probe while in acoustic contact with the abdomen of the mother until a desired anatomical orientation is in the plane of the 2D imaging probe.

Such ultrasound imaging for example may be used for screening of fetal pathologies in early gestation stages of the fetal entity (fetus), e.g. to detect an abnormal cardiac axis orientation in the fetal entity. As schematically depicted in FIG. 1, when observing the view of the fetal chest 151 at the level of the four-chamber view of the fetal heart 171, several clinical studies show that the heart axis 170 orientation can be defined with respect to an anteroposterior line 160 drawn from the spine to the anterior chest wall or sternum. This line will also be referred to as the orientation axis of the fetal chest. In this thoracic coordinate system, a normal heart axis 170 usually lies at an angle θ of approximately 45 degrees to the left (labelled L) of the anteroposterior line. Abnormal orientations correspond to the angle θ being smaller than a low angular threshold or greater than a high angular threshold. Depending on clinical studies, the low threshold value of the angle θ is defined between 25° and 30° and the high threshold value of the angle θ is defined between 59° and 65°. Unusual orientation of the heart axis 170 is an indication for an additional fetal echocardiography because it is often related to congenital heart disease and it is now recommended by the International Society of Ultrasound in Obstetrics and Gynaecology to assess the transverse chest view during the first-trimester fetal ultrasound scan in order to determine this orientation of the heart axis 170.

The first trimester fetal ultrasound scan is now a standard exam in many countries in Europe and is becoming more and more frequent in the United States, e.g. to assess the nuchal translucency within the fetal entity, which assessment may further include the aforementioned cardiac axis assessment. In order to determine the cardiac axis 170 orientation, it is commonly required to draw two lines onto an ultrasound image of the fetal chest region 151 including a view of the fetal heart 171 at the four-chamber level, which two lines correspond to the orientation axis 160 of the fetal chest and the orientation axis 170 of the fetal heart, to compute the angular value between these lines and compare it with table values.

U.S. Pat. No. 8,882,671 B2 discloses an ultrasonic diagnostic device with which volume data are collected by swing scanning in which frames in different field angle settings are mixed by a wide scan set at a wide field angle to image a diagnostic target and an index part for recognizing the position of the diagnostic target and by a narrow scan set at a field angle narrower than the field angle in the wide scan to image the diagnostic target with high time resolution. Then, the wide ultrasonic image is used to set spatial coordinates based on the index part. The spatial coordinates are used to align the narrow ultrasonic image. The diagnostic target may be a fetal entity, in which the wide field angle scan is used to identify the orientation of the spine, which is used as a mark for the determination of the orientation of the fetal heart relative to the spine.

However, this requires a number of manual inputs from the user, such as the spine position, some regions of interest and the position of the body surface. Additionally, the user has to manually define a pair of points (P and Q points) identifying the ventricular septum of the fetal heart (from here on simply referred to as septum), such that the device can calculate the orientation of the fetal heart based on the identified spinal mark and the user-defined orientation of the septum.

SUMMARY OF THE INVENTION

The present invention seeks to provide an ultrasound image processing apparatus that facilitates an automated detection of the cardiac orientation of early gestation fetal entities from a sequence of ultrasound images.

The present invention further seeks to provide an ultrasound imaging system including such an ultrasound image processing apparatus adapted to provide the ultrasound image processing apparatus with the sequence of ultrasound images.

The present invention still further seeks to provide a computer-implemented method of visualizing the orientation of the fetal heart of such a fetal entity from a received temporal sequence of ultrasound images.

The present invention still further seeks to provide a computer program product for implementing such a method on an ultrasound image processing apparatus.

According to an aspect, there is provided an ultrasound image processing apparatus comprising a processor arrangement adapted to receive a temporal sequence of ultrasound images of at least a chest region of a fetal entity from an ultrasound probe, said chest region including the fetal heart, said temporal sequence capturing at least part of a cardiac cycle of the fetal heart; identify the chest region of the fetal entity in one or more of the ultrasound images of said temporal sequence; identify a portion of the spine of said fetal entity in the identified chest region; calculate an orientation axis of the fetal chest from the identified chest region and the identified spine portion; identify the septum of the fetal heart as a linear structure which is temporally more stable than its surrounding structures in said temporal sequence of ultrasound images and which defines a region of convergence of the movements of the fetal heart during said cardiac cycle; calculate an orientation axis of the fetal heart from the identified septum; and calculate an angle between the orientation axis of the fetal chest and the orientation axis of the fetal heart.

The present invention is based on the realisation that the ventricular septum of the fetal heart can be identified in a temporal sequence of ultrasound images in which a cardiac cycle of the fetal heart is imaged as the ventricular septum typically appears in such a sequence as a (approximately) linear structure which is temporally more stable than its surrounding structures and at which the respective cardiac motions, i.e. the motions of different parts of the fetal heart during the cardiac cycle, converge. This facilitates the automatic detection of the septum from such a temporal sequence of ultrasound images, thereby obviating the need to manually identify the orientation of the septum in such ultrasound images. Consequently, the orientation angle of the fetal heart relative to the orientation axis of the fetal chest can be automatically calculated from the detection of the orientation of the fetal chest and the stable orientation of the ventricular septum throughout the cardiac cycle without users having to manually interact with the apparatus.

The processor arrangement automatically calculates the orientation axis of the fetal chest from the position of the fetal entity and the identified chest region in said one or more of the ultrasound images of the temporal sequence, which is made possible by the automatic detection of the chest region and the spinal portion of the fetal entity, e.g. using shape transform and machine learning algorithms, thereby obviating the need to manually provide markers to identify such structures. In an embodiment, the processor arrangement automatically calculates the orientation axis of the fetal chest from the position of the fetal entity and the identified chest region in the ultrasound image in which the heart orientation is calculated.

In a preferred embodiment, the processor arrangement further is adapted to generate a control signal for a display device, said control signal causing the display device to visualize at least one of said ultrasound images on a display screen of the display apparatus; and generate an overlay over the at least one of said ultrasound images on said display screen, said overlay visualizing the orientation axis of the fetal heart in its calculated orientation. Such visualization of the orientation of the fetal heart within the chest region of the fetus facilitates an intuitive interpretation of the fetal scan results by a user of the ultrasound image processing apparatus when coupled to a display device onto which the scan results are visualized.

For example, the control signal may further cause the display device to visualize the orientation axis of the fetal heart on the display screen as a function of the value of the angle between the calculated orientation of the orientation axis of the fetal chest and the calculated orientation of the orientation axis of the fetal heart. Such angle-dependent visualization facilitates an intuitive recognition of whether the angle is indicative of the fetal entity having an increased likelihood of suffering from congenital heart disease, for instance by representing the axis of the fetal heart in a different manner when its orientation angle is indicative of such an increased likelihood compared to representing the axis of the fetal heart when its orientation angle lies within a range of values considered to be normal values of this orientation.

In an embodiment, the control signal further causes the display device to visualize the orientation axis of the fetal heart in its calculated orientation within a first sector on the display screen visualizing a defined range of values of said angle if the value of said angle is within said defined range and within a second sector on the display screen if the value of said angle is outside said defined range. Such different sectors typically are indicative of the orientation of the fetal heart lying within or outside a range of values considered to be normal values of this orientation.

Preferably, the first sector is visualized in a first colour and the second sector is visualized in a second colour different to the first colour such that a user of the ultrasound image processing apparatus is presented with colour information indicative of whether the orientation of the fetal heart lies within or outside a range of values considered to be normal values of this orientation, which allows for an intuitive and straightforward interpretation of the scan results, i.e. of the orientation of the fetal heart within the fetal entity.

In an alternative embodiment, the control signal further causes the display device to visualize the orientation axis of the fetal heart in its calculated orientation in a first colour on said display screen if the value of said angle is within a defined range of values for said angle and in a second colour on said display screen if the value of said angle is outside said defined range. This is an alternative manner of presenting such scan results using colour coding in order to facilitate intuitive and straightforward interpretation of these results.

Further colour coding may be used to refine the presentation of such scan results. For example, the control signal may further cause the display device to visualize the orientation axis of the fetal heart in its calculated orientation in a third colour on said display screen if the value of said angle is within a defined distance from an endpoint of said range of values for said angle. In this manner, orientations of the fetal heart relative to the orientation of the fetal chest that are considered borderline orientations may be visually highlighted, which information for example may be used by a user of the ultrasound image processing apparatus to initiate a further investigation, e.g. further ultrasound scans, of the fetal entity in order to scrutinize the orientation of the fetal heart relative to the fetal chest and the heart anatomy and function themselves in more detail.

The ultrasound image processing apparatus may be adapted to provide such control signals to separate display device that may be coupled to the ultrasound image processing apparatus in any suitable manner. Alternatively, the ultrasound image processing apparatus may further comprise the display device communicatively coupled to the processor arrangement. For example, the display device may form an integral part of the ultrasound image processing apparatus.

According to another aspect, there is provided an ultrasound imaging system comprising the ultrasound image processing apparatus of any of the herein described embodiments and an ultrasound probe for providing the ultrasound image processing apparatus with the temporal sequence of ultrasound images of at least a chest region of a fetal entity. Such an ultrasound probe may be any suitable ultrasound probe, e.g. an ultrasound probe capable of generating a sequence of 2-D or 3-D ultrasound images (volumetric images), which ultrasound probe may be coupled to the ultrasound image processing apparatus in any suitable manner, e.g. in a wired or wireless fashion.

According to yet another aspect, there is provided a computer-implemented method for visualizing an orientation of the heart of a fetal entity within said entity, the method comprising receiving a temporal sequence of ultrasound images of at least a chest region of a fetal entity from an ultrasound probe, said chest region including the fetal heart, said temporal sequence capturing at least part of a cardiac cycle of the fetal heart; identifying the chest region of the fetal entity in one or more of the ultrasound images of said temporal sequence; identifying a portion of the spine of said fetal entity in the identified chest region; calculating an orientation axis of the fetal chest using the identified chest region and the identified spine portion; identifying the septum of the fetal heart as a linear structure which is temporally more stable than its surrounding structures in said temporal sequence of ultrasound images and which defines a region of convergence of the movements of the fetal heart during said cardiac cycle; calculating an orientation axis of the fetal heart from the identified septum; calculating an angle between the orientation axis of the fetal chest and the orientation axis of the fetal heart; and generate a control signal for a display device, said control signal causing the display device to visualize at least one of said ultrasound images on a display screen of the display apparatus and generate an overlay over the at least one of said ultrasound images on said display screen, said overlay visualizing the orientation axis of the fetal heart in its calculated orientation.

Such an automated visualization of the orientation of the fetal heart relative to the fetal spine facilitates a straightforward interpretation of the temporal sequence ultrasound images without requiring user input to obtain this orientation, such that relatively inexperienced users of an ultrasound image processing apparatus implementing this method can interpret the obtained orientation of the fetal heart.

Preferably, the control signal further causes the display device to visualize the orientation axis of the fetal heart on the display screen as a function of the value of the angle between the calculated orientation of the orientation axis of the fetal chest the calculated orientation of the orientation axis of the fetal heart such that the user can immediately recognize if the calculated angle has an abnormal value.

In an example embodiment, the control signal further causes the display device to visualize the orientation axis of the fetal heart in its calculated orientation within a first sector on the display screen visualizing a defined range of values of said angle if the value of said angle is within said defined range and within a second sector on the display screen if the value of said angle is outside said defined range, preferably wherein the first sector is visualized in a first colour and the second sector is visualized in a second colour different to the first colour. Optionally, the control signal further causes the display device to visualize the orientation axis of the fetal heart in its calculated orientation within a third sector on the display screen visualizing a defined range of values of said angle if the value of said angle is within a defined distance from an endpoint of said range of values for said angle, wherein the third sector is visualized in a third colour different to the first and second colours.

In an alternative example embodiment, the control signal further causes the display device to visualize the orientation axis of the fetal heart in its calculated orientation in a first colour on said display screen if the value of said angle is within a defined range of values for said angle and in a second colour on said display screen if the value of said angle is outside said defined range, optionally wherein the control signal further causes the display device to visualize the orientation axis of the fetal heart in its calculated orientation in a third colour on said display screen if the value of said angle is within a defined distance from an endpoint of said range of values for said angle.

These example embodiments allow a user to immediately recognize if the value of the angle between the fetal heart orientation axis and the chest orientation axis has an abnormal value as well as to recognize if this angle has a borderline value warranting further investigation as previously explained.

According to another aspect, there is provided a computer program product comprising a computer readable storage medium having computer readable program instructions embodied therewith for, when executed on a processor arrangement of an ultrasound image processing apparatus, causes the processor arrangement to implement the method of any of the herein described embodiments. Consequently, an existing ultrasound imaging processing apparatus may be reconfigured or upgraded using such a computer program product to implement the method of the present invention.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
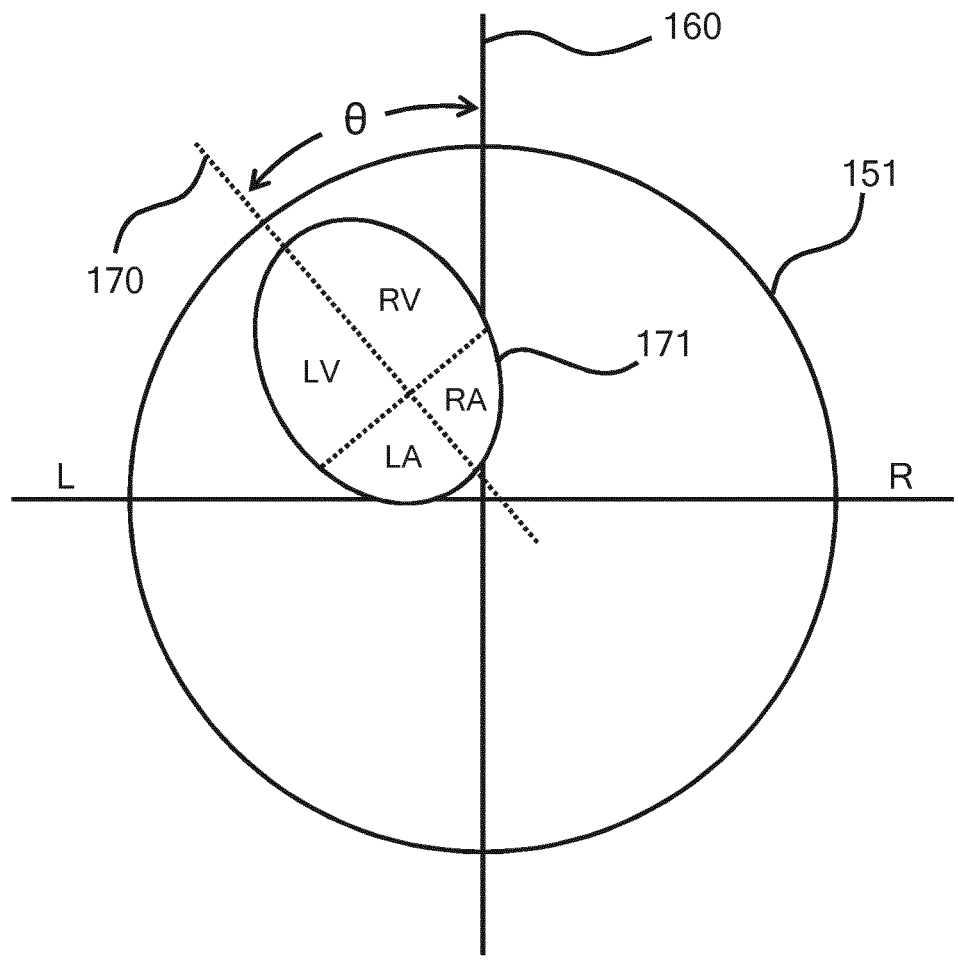
FIG. 1 schematically depicts a diagram explaining the relative orientation of the heart of a fetal entity in its chest region.

It should be understood that the Figures are merely schematic and are not drawn to scale. It should also be understood that the same reference numerals are used throughout the Figures to indicate the same or similar parts.

Figure 2:
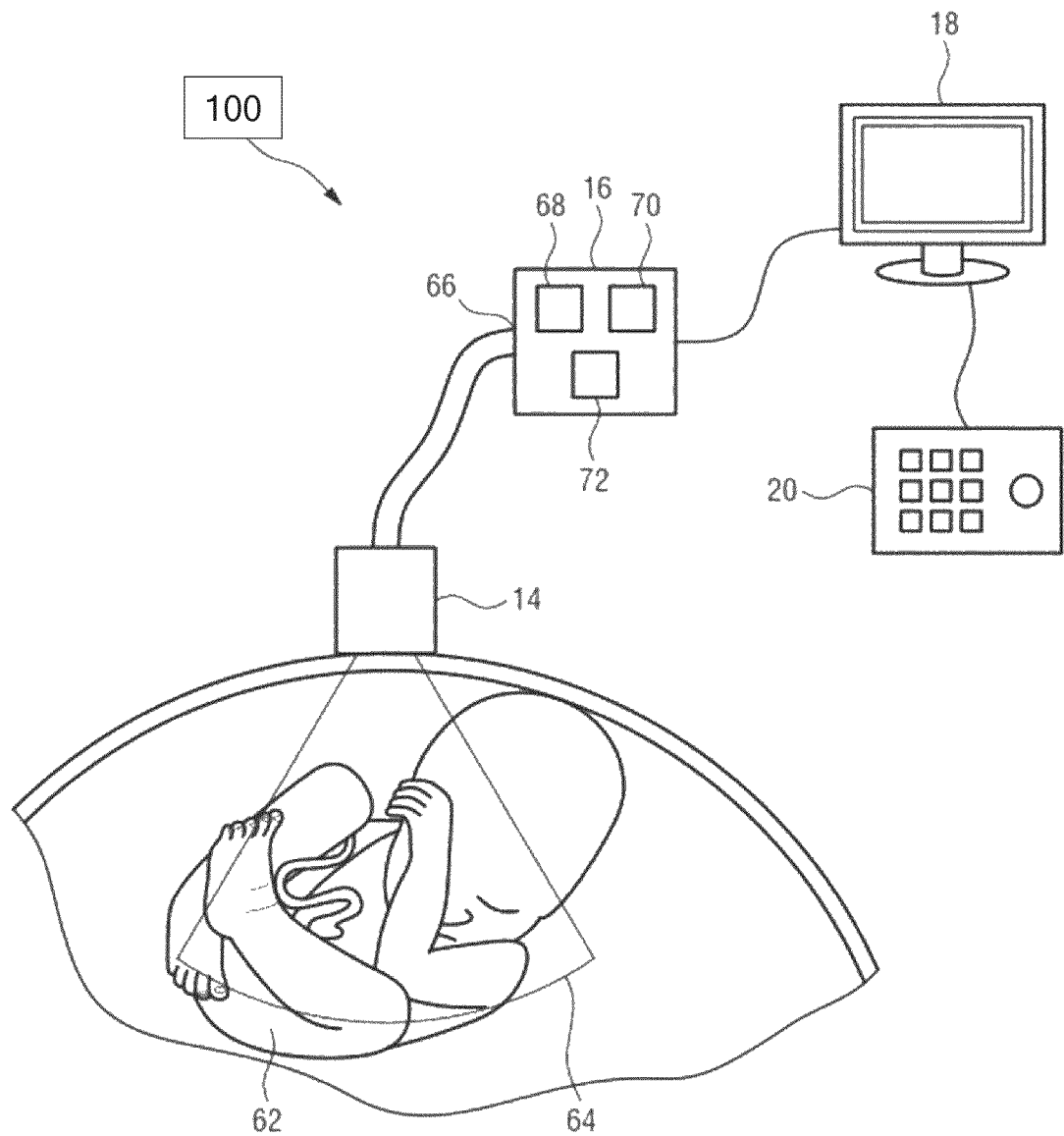
FIG. 2 shows a schematic diagram of an ultrasound image processing apparatus according to an embodiment.

FIG. 2 shows a schematic illustration of an ultrasound imaging system 100, in particular a medical two-dimensional (2D) ultrasound imaging system or three-dimensional (3D) ultrasound imaging system. The ultrasound system 100 may be applied to inspect a volume of an anatomical site. For example, the ultrasound imaging system 100 scans by means of the ultrasound probe 14 a fetus, which is generally denoted by 62. The ultrasound probe 14 scans an anatomical site, which forms a region of interest (ROI) and which is generally denoted by 64. The ultrasound probe 14 may have at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements may be arranged in a linear array in case of a 2D ultrasound system 100 or may be arranged in a two-dimensional array, in particular for providing a multi-planar or three-dimensional image in case of a 2D ultrasound system 100. In general, (matrix) transducer systems as found on Philips iE33 systems or mechanical 3D/4D transducer technology as found, for example, on the Philips EPIQ and Affiniti systems, e.g. including a mechanical V6-2 probe, may be applied in conjunction with the current invention.

In embodiments of the present invention, the ROI 64 includes a chest region of the fetus 62, in which the fetal heart is captured, as will be explained in more detail below. The ultrasound probe 14 may be connected to an ultrasound image processing apparatus 16 via an ultrasound data interface 66, which may be wired or wireless interface. The ultrasound image processing apparatus 16 may comprise a segmentation unit 68, an orientation detection unit 70 and a calculation unit 72. It should be understood that such units may be implemented in any suitable manner, e.g. by one or more suitably configured processors, which will also be referred to in the present application as a processor arrangement, i.e. an arrangement of one or more processors adapted to implement the functionality of the segmentation unit 68, the orientation detection unit 70 and the calculation unit 72 as described in more detail below.

The ultrasound image processing apparatus 16 may be connected to a display device 18 (simply referred to as display 18 in the remainder) for displaying the results of the ultrasound scan and which is connected to an input device or user interface 20 for inputting instructions to control the ultrasound imaging system 100. The display 18 may be separate to the ultrasound image processing apparatus 16 or may form part of the ultrasound image processing apparatus 16, e.g. may be integrated into the ultrasound image processing apparatus 16. The input device 20 may comprise keys or a keyboard and further inputting devices, for example a trackball or a mouse. The input device 20 may be connected to the display 18 or directly to the ultrasound image processing apparatus 16.

In this example embodiment, the ultrasound image processing apparatus 16 may receive a temporal sequence of ultrasound images, e.g. 2-D images or 3-D images directly from the ultrasound probe 14. However, it should be understood that it is equally feasible for the ultrasound image processing apparatus 16 to retrieve the temporal sequence of ultrasound images from a data storage arrangement (not shown) such as a local or remote data storage device into which the temporal sequence of ultrasound images was temporarily stored to facilitate 'off-line' evaluation of the scan results, e.g. after completion of the investigation of the female patient carrying the fetus 62. The data storage arrangement for example may include one or more memory devices, hard disks, optical discs, or the like, in which the ultrasound image processing apparatus 16 may store image frames and image frame processing data, e.g. for evaluation at a later date.

The segmentation unit 68 is provided for segmenting anatomical structures of the fetus 62 in the 2D or 3D ultrasound data captured by the ultrasound probe 14 and the segmentation unit 68 provides segmentation data of the anatomical structures of the fetus 62. The orientation detection unit 70 may be provided for detecting the relative orientation of target anatomical structures of the fetus 62 based on the segmentation data provided by the segmentation unit 68, e.g. within a defined coordinate system such as a thoracic coordinate system. For example, the orientation detection unit 70 may be configured to detect the orientation axis 160 of the fetal spine and the orientation axis 170 of the fetal heart as will be explained in further detail below.

The calculation unit 72 may be configured to calculate the angle θ between the orientation axis 160 of the fetal chest and the orientation axis 170 of the fetal heart 171 at a determined by the orientation detection unit 170 and to generate a control signal for the display 18 in order to display the calculation result onto the display screen of the display 18, e.g. as an overlay over an ultrasound image from said temporal sequence of ultrasound images such that the position of the fetal heart 171 in the chest region 151 of the fetus 62 is visualized by this overlay. In a preferred embodiment, the displayed ultrasound image is a 2-D ultrasound image, which in case of a temporal sequence of volumetric ultrasound images (i.e. 3-D ultrasound images) may be generated by extracting a volume slice from such a volumetric image, e.g. using the user interface 20, as is well-known per se.

Figure 3:
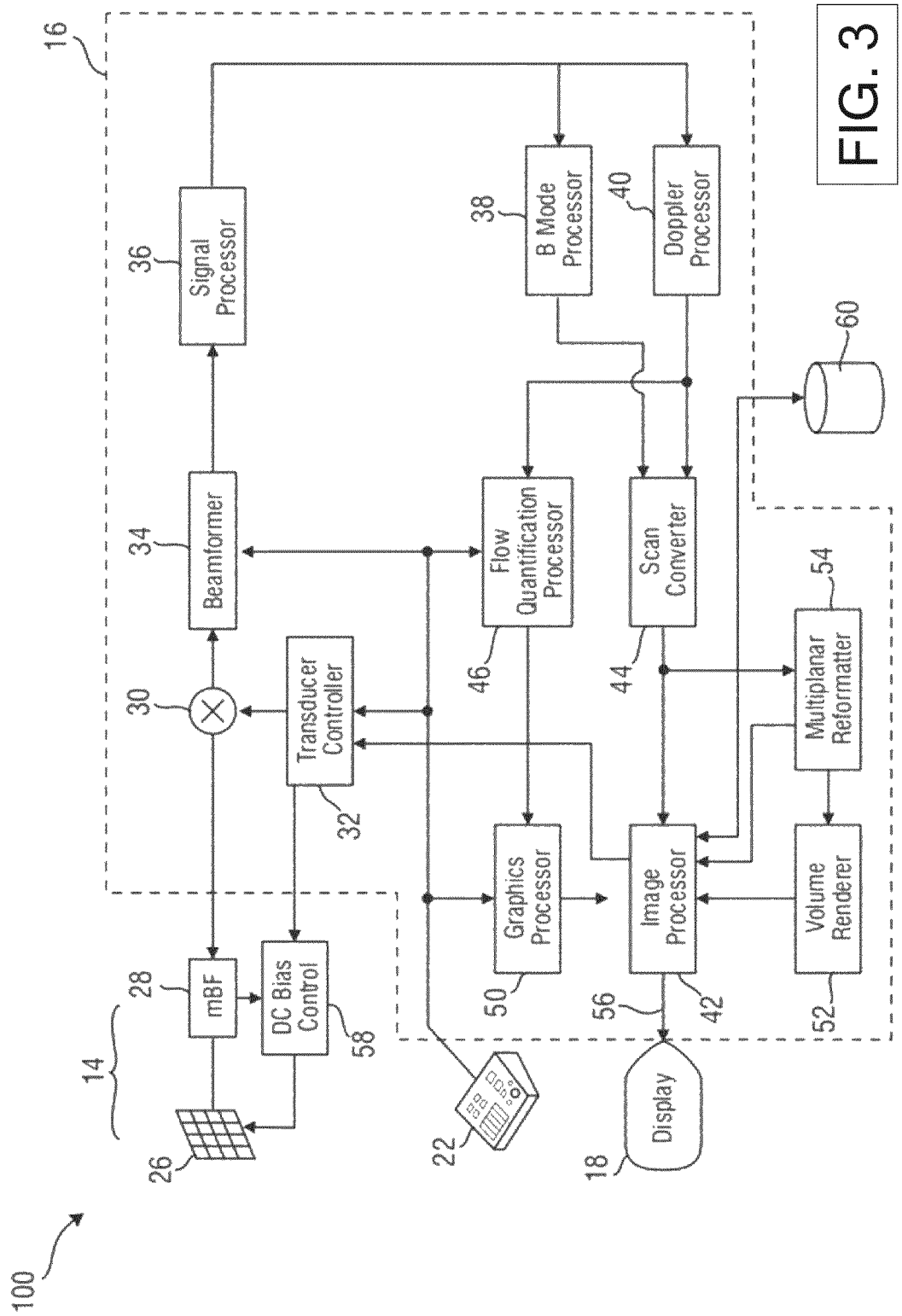
FIG. 3 shows a schematic block diagram of an embodiment of an ultrasound imaging system with an array transducer according to an embodiment.

FIG. 3 illustrates a schematic block diagram of an example embodiment of the ultrasound imaging system 100 including the ultrasound probe 14 and the ultrasound image processing apparatus 16. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements, optionally associated with a mechanical sweep mechanism, capable of scanning in two dimensions for 2D imaging or in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient, e.g. a pregnant female patient. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field.

In a 3D imaging system, the multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18. The image processor 42 may form part of any type of imaging system (e.g. a 2D or 3D imaging system) and in at least some embodiments may implement at least part of the processor arrangement as described in the present application.

In addition to being used for imaging, the blood flow values produced by the Doppler processor 40 and tissue structure information produced by the B mode processor 38 may be transferred to a quantification processor 46 forming part of the processor arrangement. This quantification processor 46 may produce measures of different flow conditions such as the volume rate of blood flow. The quantification processor 46 optionally may receive input from the user control panel 22, such as the point in the anatomy of an image where a measurement is to be made, in case a user of the ultrasound imaging system 100 is interested in obtaining biometric measurements of an anatomical feature of interest of the fetus 62. Output data from the quantification processor 46 may be transferred to a graphics processor 50 forming part of the processor arrangement of the ultrasound image processing apparatus 16.

The graphics processor 50 can also generate graphic overlays for display with the ultrasound images. These graphic overlays can contain standard identifying information such as patient name, date and time of the image, imaging parameters, and the like, as will be explained in more detail below. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images in case of a 3D imaging system.

Again, it shall be noted that the aforementioned ultrasound image processing apparatus 16 described as part of the ultrasound imaging system 100 has only been explained as one possible example for an application of the ultrasound image processing apparatus 16. It shall be noted that the aforementioned ultrasound image processing apparatus 16 does not have to comprise all of the components explained before. On the other hand, the ultrasound image processing apparatus 16 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities as schematically shown in FIG. 3.

Figure 4:
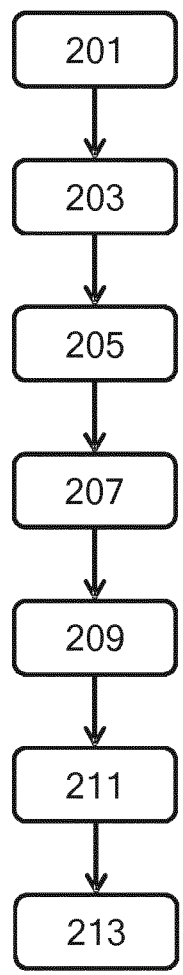
FIG. 4 depicts a flowchart of a computer-implemented method according to an embodiment.
Figure 5:
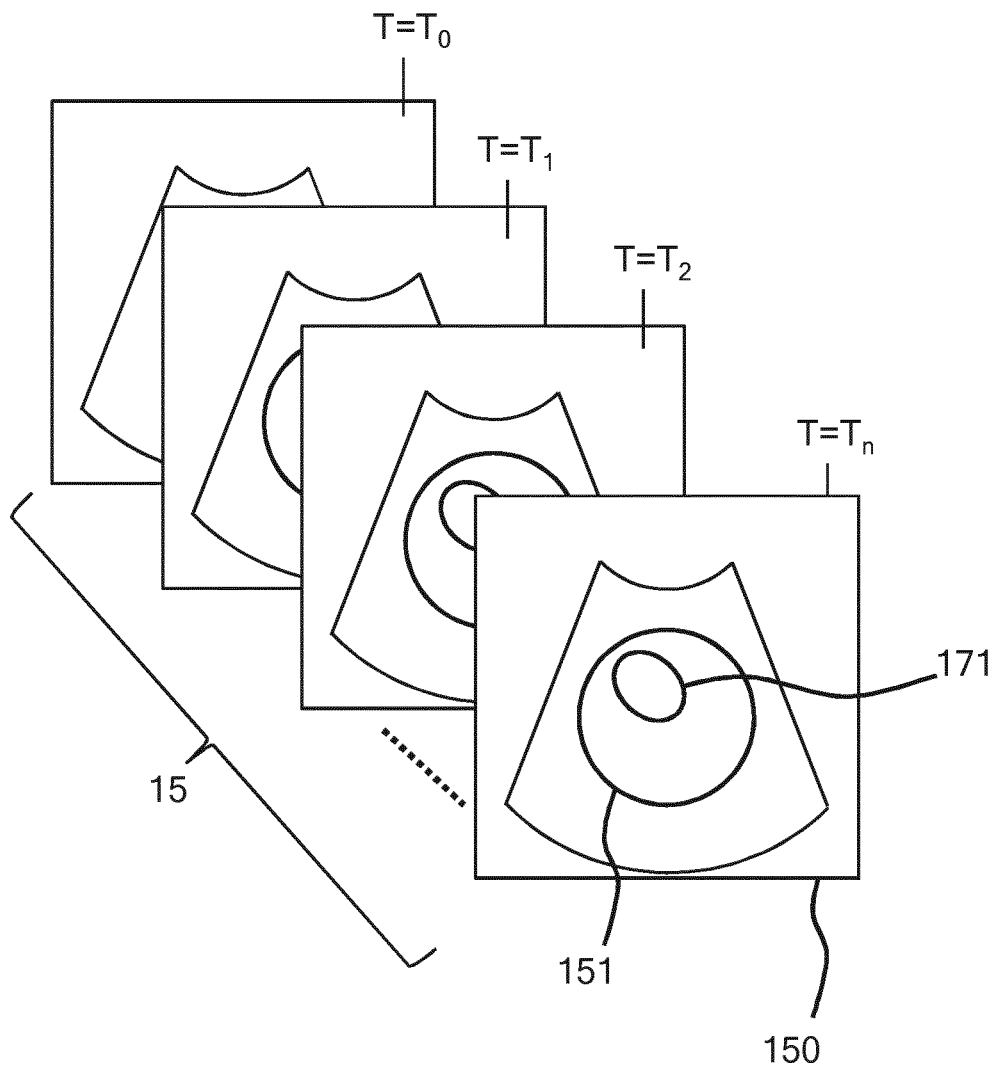
FIG. 5 schematically depicts a temporal sequence of ultrasound images for processing by an ultrasound image processing apparatus according to an embodiment.

The processor arrangement of the ultrasound image processing apparatus 16 is adapted to automatically determine the orientation of the fetal heart 171 in the chest region 151 of the fetal entity 62. This will be further explained with the aid of FIG. 4, which depicts a flowchart of a method 200 implemented by this processor arrangement. In operation 201, the processor arrangement of the ultrasound image processing apparatus 16 receives a temporal sequence 15 of ultrasound images 150 as schematically depicted in FIG. 5. In the context of the present application, a temporal sequence 15 of ultrasound images 150 refers to a sequence of ultrasound images in which the same anatomical region of interest is imaged over a period of time (as depicted in FIG. 5 by the different time labels $T=T_0, T=T_1, T=T_2, T=T_n$), such that the sequence comprises a plurality of ultrasound images in which changes over time in the anatomical region of interest can be visualized. This for example is particularly useful where the temporal sequence 15 of ultrasound images 150 image a fetal chest region 151 including the fetal heart 171 such that at least part of the cardiac cycle and preferably at least a full cardiac cycle of the fetal heart 171 is captured by the temporal sequence 15 of ultrasound images 150, as this facilitates determination of the orientation of the fetal heart 171 in the chest region 151 of the fetal entity 62 as will be explained further below. To this end, the temporal sequence 15 of ultrasound images 150 preferably comprises ultrasound images in which a four-chamber view of the fetal heart 171 is provided, such that the ventricular septum can be clearly identified in these images.

The processor arrangement of the ultrasound image processing apparatus 16 may receive the temporal sequence 15 of ultrasound images 150 directly from an ultrasound probe 14 or alternatively may receive the temporal sequence 15 of ultrasound images from a data storage arrangement into which the temporal sequence 15 of ultrasound images 150 was previously stored, e.g. by the ultrasound image processing apparatus 16 for processing at a later date. The temporal sequence 15 of ultrasound images 150 may consist of a sequence of 2-D ultrasound image frames, which may be acquired with a 2-D ultrasound probe 14 or alternatively the temporal sequence 15 of ultrasound images 150 may be generated from a sequence of volumetric ultrasound images by extracting a particular 2-D ultrasound image slice from such a volumetric image in which the chest region 151 including the fetal heart 171 are clearly imaged, e.g. in which a four-chamber view of the fetal heart 171 is provided.

Figure 6:
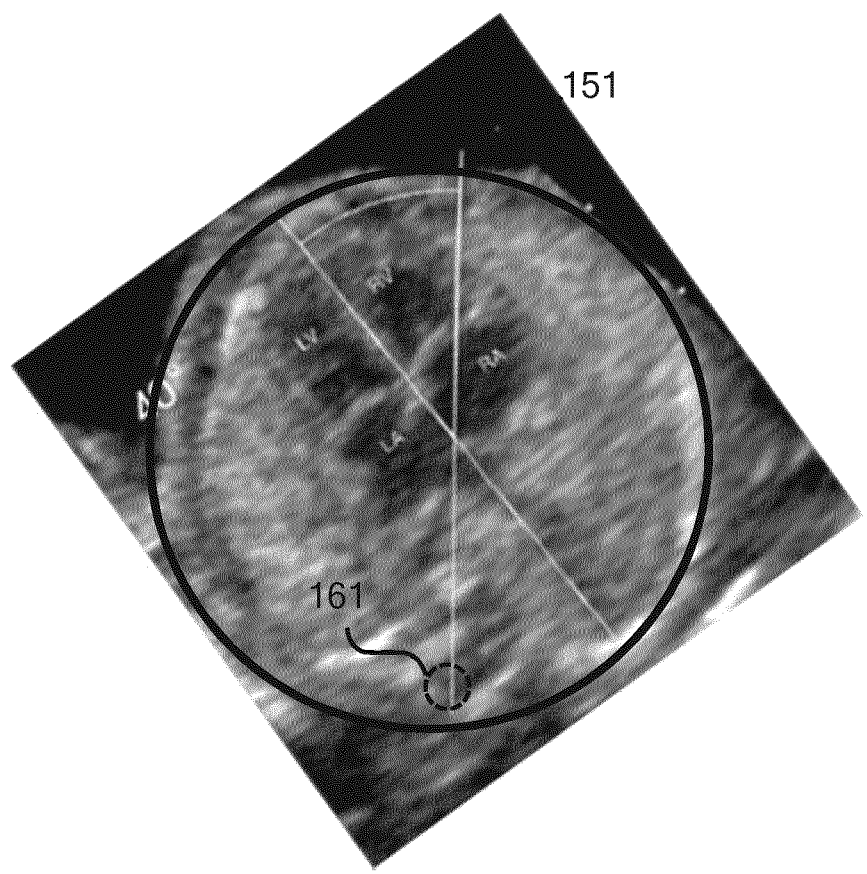
FIG. 6-8 schematically depict different processing steps of such a temporal sequence of ultrasound images by an ultrasound image processing apparatus according to an embodiment.

The processor arrangement, e.g. the segmentation unit 68, first calculates the orientation axis 160 of the fetal chest in a defined coordinate system from the temporal sequence 15 of ultrasound images 150, as schematically depicted in FIG. 6. This calculation may be performed on one or more of the ultrasound images 150 of the temporal sequence 15. In operation 203, the processor arrangement, e.g. the segmentation unit 68, delineates the chest region 151 of the fetal entity 62 in one or more of the ultrasound images 150 of said temporal sequence 15. Any suitable segmentation algorithm, such as for example a Hankel transformation algorithm and a deformable contour segmentation algorithm may be used for this purpose. As such algorithms are well-known per se, this will not be explained in further detail for the sake of brevity only.

In operation 205, the processor arrangement for example may be arranged to recognize a vertebrae structure 161, e.g. a part of the fetal spine, within the delineated fetal chest region 151 in such ultrasound images 150 as schematically depicted in FIG. 6. The ultrasound image processing apparatus 16 may be trained to develop this functionality using machine learning algorithms such as a random forest algorithm, a deep learning approach or any other suitable learning method in which the processor arrangement is presented with a plurality of fetal images from which the fetal position and associated position of the fetal chest region and the portion of the fetal spine within the fetal chest region is identified.

Figure 7:
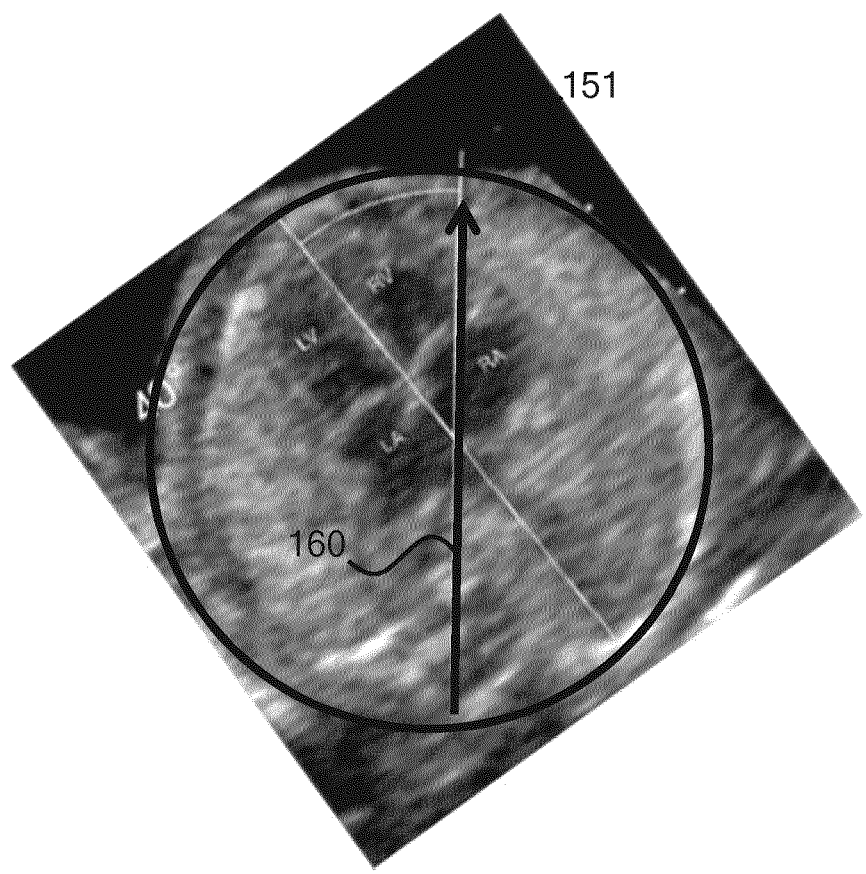

The detection of the spine position in operation 205 and the delineated chest region 151 in operation 203 may be combined to perform a constrained ellipse fitting on the delineated chest region 151, e.g. with the orientation detection unit 170. The ellipse fitting is done such that the ellipse position is as close as possible to the border of the delineated chest region 151, while one axis of the ellipse is constrained to go through the detected vertebrae structure 161. This ellipse axis corresponds to the anteroposterior line between the vertebrae and the septum, which line defines the orientation axis 160 of the fetal chest as schematically depicted in FIG. 7. In an embodiment, the orientation axis 160 defines the vertical axis of a coordinate system such as a thoracic coordinate system in a visualization mode of the method 200, e.g. for the purpose of intuitive visualization of the orientation of the fetal heart 171 within the chest region 151 as will be explained in more detail below.

In operation 207, the processor arrangement, e.g. the segmentation unit 68, of the ultrasound image processing apparatus 16 identifies the septum of the fetal heart 171 as a temporally stable linear structure in the temporal sequence 15 of ultrasound images 150, i.e. as a linear structure that temporally is more stable than its surrounding structures in the temporal sequence 15. More specifically, the temporal sequence 15 of ultrasound images 150 captures at least part of the cardiac cycle of the fetal heart 171 such that the movements, e.g. contractions and expansions, of the fetal heart 171 associated with the cardiac cycle, i.e. with the pumping function, of the fetal heart 171 are captured in the temporal sequence 15. The processor arrangement of the ultrasound image processing apparatus 16 typically is arranged to evaluate such movements across the temporal sequence 15 and to identify a linear region within the fetal heart 171 that remains more stable than its surrounding structures during the various stages of the cardiac cycle as captured by the temporal sequence 15, and which defines a region of convergence for these movements. This region can be identified by evaluating the direction of movement of various points along the perimeter of the fetal heart 171 during its cardiac cycle, in which the respective directions of these movements at least approximately converge in a more stable region within the fetal heart 171, which more stable region typically approximates the position of the ventricular septum of the fetal heart 171.

Figure 8:
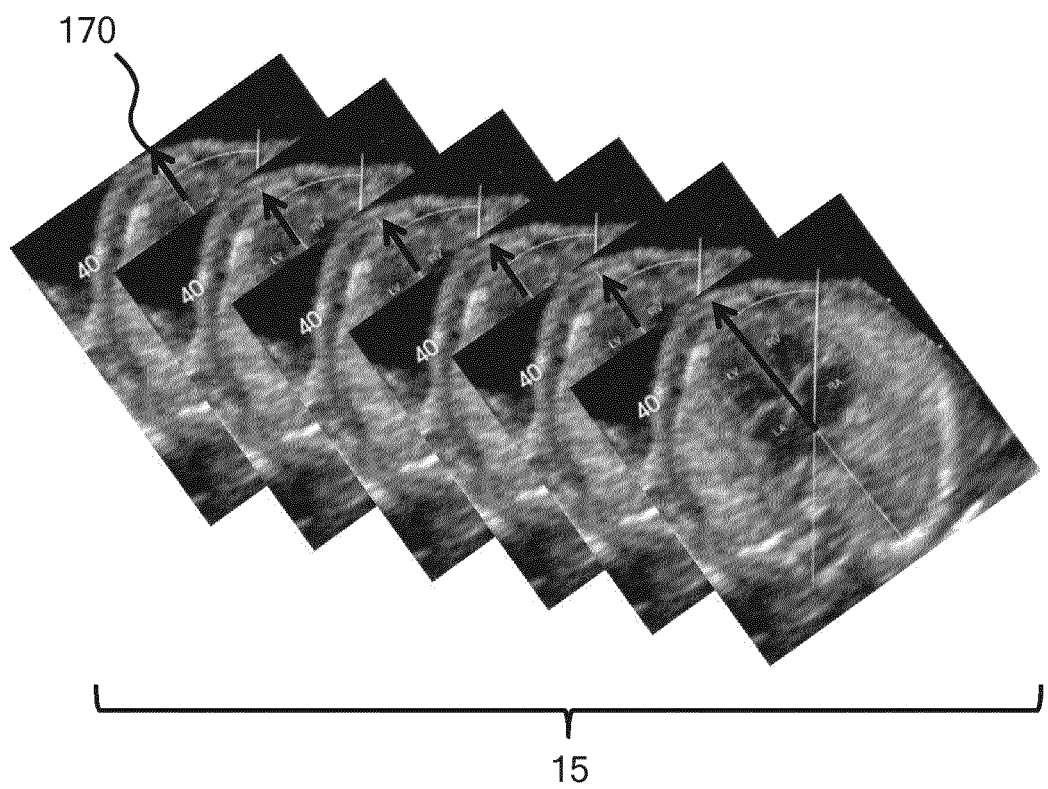

As the ventricular septum of the fetal heart 171 typically lies on or close to the orientation axis of the fetal heart 171, the thus identified more stable linear region within the fetal heart 171 during its cardiac cycle may be used to accurately estimate the relative orientation of the fetal heart 171 within the chest region 151 of the fetal entity 62. Thus, in operation 209, the processor arrangement of the ultrasound image processing apparatus 16, e.g. the orientation detection unit 70, calculates the orientation axis 170 of the fetal heart 171 from the identified temporally 'stable' linear region within the fetal heart 171, i.e. from the identified ventricular septum of the fetal heart 171, throughout the temporal sequence 15 of ultrasound images 150, i.e. during its cardiac cycle, as schematically depicted in FIG. 8.

At this stage, the calculation unit 172 of the ultrasound image processing apparatus 16 can calculate the angle between the identified orientation axis 160 of the fetal chest and the identified orientation axis 170 of the fetal heart 171 in operation 211, thereby providing an automated calculation of the orientation of the fetal heart 171 in the chest region 151 of the fetal entity 62 relative to the orientation of the fetal chest, i.e. the orientation angle θ, from which it can be determined if the fetal entity 62 is likely to suffer from congenital heart disease as previously explained, without a user of the ultrasound image processing apparatus 16 having to manually identify markers from which the orientation of the fetal heart 171 have to be determined.

In a preferred embodiment, the ultrasound image processing apparatus 16 is further adapted, e.g. through its graphics processor 50, to generate a control signal for the display 18 in operation 213 of the method 200, which control signal causes the display 18 to generate an overlay over an ultrasound image 150 from the temporal sequence 15, e.g. a 2-D ultrasound image frame, to visualize the orientation axis 170 of the fetal heart 171 in a defined coordinate system such as a thoracic coordinate system as previously explained on its display screen. Consequently, a user of the ultrasound image processing apparatus 16 can immediately recognize whether the orientation angle θ of the fetal heart axis 170 is normal or abnormal.

This assessment to be made by the user may be further aided by the control signal causing the display 18 to generate different appearances of the overlay on its display screen as a function of the value of the orientation angle θ of the fetal heart axis 170, e.g. using a colour coding scheme in which the overlay has a first colour indicating an normal value of the orientation angle θ of the fetal heart axis 170 and has a second colour indicating an abnormal value of the orientation angle θ of the fetal heart axis 170, such that the user of the ultrasound image processing apparatus 16 can immediately recognize from the displayed colour whether the value of the orientation angle θ of the fetal heart axis 170 lies within a defined range of values of the orientation angle θ, i.e. a range of values indicative of a normal value of this orientation angle. Such a range of values is defined by a lower end point and a higher end point, which endpoints may be selected in accordance with generally accepted threshold values of the angle θ, i.e. a lower endpoint between 25° and 30° and a higher endpoint between 59° and 65° as previously explained.

Whether the orientation angle θ of the fetal heart axis 170 lies within such a range may be visualized in any suitable manner. In a first example implementation, the control signal may cause the display 18 to display a numerical value of the orientation angle θ on its display screen, optionally together with the fetal heart axis 170 in its calculated orientation overlaying the displayed ultrasound image 150, which displayed numerical value may be displayed using the first colour when the numerical value is considered a normal value, or may be displayed using the second colour when the numerical value is considered an abnormal value, such that the user can interpret the colour of the displayed numerical value in order to determine whether the fetal heart 171 lies in a normal or abnormal orientation.

Figure 9:
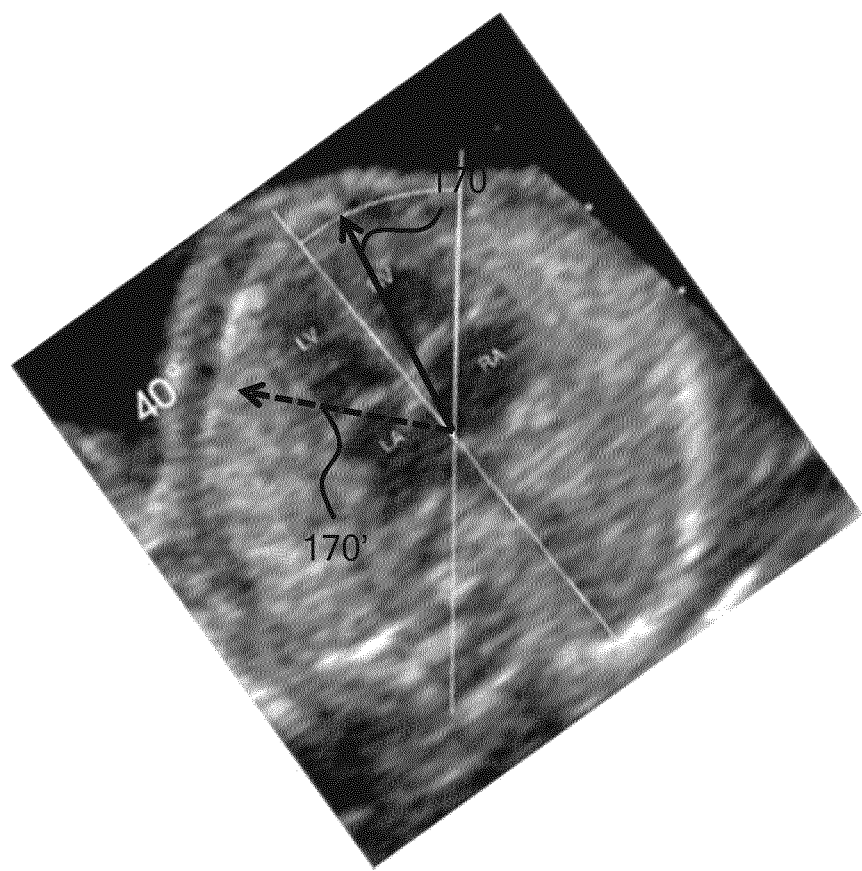
FIG. 9 schematically depicts a visualization mode of a processing result of the ultrasound image processing apparatus according to an embodiment.

In another example embodiment as schematically depicted in FIG. 9, the orientation axis 170 visualized as an overlay over the ultrasound image 150 on the display screen of the display 18 itself may be colour-coded, such that the orientation axis 170 is visualized in the first colour when the numerical value is considered a normal value, and this visualized in the second colour when the numerical value is considered an abnormal value, here schematically depicted by the dashed orientation axis 170'. This has the advantage that the user does not have to interpret the numerical value of the orientation angle θ but instead simply can rely on the manner, e.g. the colour, in which the orientation axis 170 is displayed as an overlay over the displayed ultrasound image 150.

In a refinement of this embodiment, the orientation axis 170 may be visualized in a third colour if the value of the orientation angle θ lies within a defined distance from an endpoint of the range of values defining a normal value of this orientation angle. This for example may be used to flag borderline values of the orientation angle θ, which may be used to trigger further investigation of the orientation of the heart 171 of the fetal entity 62, e.g. further ultrasound scans at a higher resolution or other types of diagnostic testing, in order to further investigate whether the fetal entity 62 suffers from cardiac abnormalities such as congenital heart disease.

Figure 10:
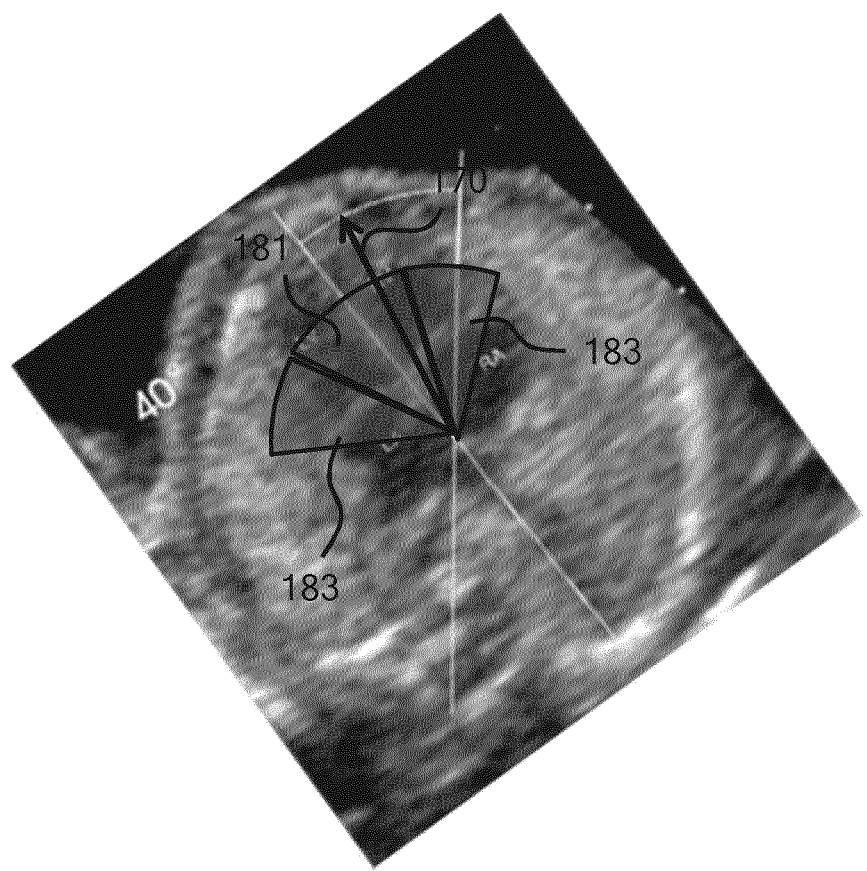
FIG. 10 schematically depicts another visualization mode of a processing result of the ultrasound image processing apparatus according to an embodiment.

FIG. 10 schematically depicts another example embodiment of the visualization of the orientation axis 170 as an overlay over the displayed ultrasound image 150 on the display 18. In this embodiment, the control signal generated by the processor arrangement, e.g. the graphics processor 50, of the ultrasound image processing apparatus causes the display 18 to generate different sectors 181, 183, e.g. differently coloured sectors in which the orientation axis 170 is visualized, e.g. using a contrasting colour. The first sector 181 for example may be visualized in the first colour and may indicate the defined range of values of the orientation angle θ, i.e. a range of values indicative of a normal value of this orientation angle, whereas the sectors 183 may indicate further ranges of values of the orientation angle θ, i.e. ranges of values indicative of an abnormal value of this orientation angle. As before, this may be further refined by having intermediate sectors (not shown) in between the sectors 181 and 183 that indicate borderline values of the orientation angle θ and that are shown in a third colour to distinguish them from the sectors 181 and 183. Further variations to this embodiment may be immediately apparent to the skilled person. For example, only the sector in which the orientation axis 170 lies may be visualized or alternatively the sector 181 is always shown and a sector 183 is only shown if the orientation axis 170 lies in this sector.

The above described embodiments of the method 200 may be realized by computer readable program instructions embodied on a computer readable storage medium having, when executed on a processor arrangement of the ultrasound image processing apparatus 16, cause the processor arrangement to implement the method 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like.

The computer readable storage medium may be an Internet-accessible service from which the computer readable program instructions may be obtained. In an embodiment, an ultrasound image processing apparatus 16 is adapted to retrieve the computer readable program instructions from such a computer readable storage medium and to create a new computer readable storage medium by storing the retrieved computer readable program instructions in a data storage arrangement, e.g. in a memory device or the like forming part of the data storage arrangement, which data storage arrangement is accessible to the processor arrangement of the ultrasound image processing apparatus 16 such that the processor arrangement can retrieve the computer-readable program instructions from the data storage arrangement for execution.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound image processing apparatus comprising a processor arrangement adapted to:
   receive a temporal sequence of ultrasound images of at least a chest region of a fetal entity from an ultrasound probe, said chest region including the fetal heart, said temporal sequence having captured at least part of a cardiac cycle of the fetal heart;
   identify the chest region of the fetal entity in one or more of the ultrasound images of said temporal sequence;
   identify a portion of the spine of said fetal entity in the identified chest region;
   calculate an orientation axis of the fetal chest from the identified chest region and the identified spine portion;
   identify the septum of the fetal heart as a linear structure that is temporally more stable than its surrounding structures in said temporal sequence of ultrasound images and that defines a region of convergence of movements of the fetal heart during said cardiac cycle;
   calculate an orientation axis of the fetal heart from the identified septum;
   calculate an angle between the orientation axis of the fetal chest and the orientation axis of the fetal heart; and
   generate a control signal for a display device, said control signal causing the display device to (i) visualize at least one of said ultrasound images on a display screen of the display apparatus; and (ii) generate an overlay over the at least one of said ultrasound images on said display screen, said overlay comprising the axis of the fetal heart in its calculated orientation, wherein the orientation axis of the fetal heart on the display screen is displayed as a function of the value of the calculated angle between the orientation axis of the fetal chest and the orientation axis of the fetal heart.

2. The ultrasound image processing apparatus of claim 1, wherein the processor arrangement is adapted to calculate the orientation axis of the fetal chest from the position of the fetal entity and the identified chest region in said one or more of the ultrasound images of the temporal sequence.

3. The ultrasound image processing apparatus of claim 1, wherein the control signal further causes the display device to visualize the orientation axis of the fetal heart in its calculated orientation within a first sector on the display screen comprising a defined range of values of said angle if the calculated value of said angle is within said defined range and within a second sector on the display screen if the value of said angle is outside said defined range.

4. The ultrasound image processing apparatus of claim 3, wherein the first sector is visualized in a first colour and the second sector is visualized in a second colour different to the first colour.

5. The ultrasound image processing apparatus of claim 1, wherein the control signal further causes the display device to visualize the orientation axis of the fetal heart in its calculated orientation in a first colour on said display screen if the value of said angle is within a defined range of values for said angle and in a second colour on said display screen if the value of said angle is outside said defined range.

6. The ultrasound image processing apparatus of claim 5, wherein the control signal further causes the display device to visualize the orientation axis of the fetal heart angle in its calculated orientation in a third colour on said display screen if the value of said angle is within a defined distance from an endpoint of said range of values for said angle.

7. The ultrasound image processing apparatus of claim 1, further comprising the display device communicatively coupled to the processor arrangement.

8. An ultrasound imaging system comprising the ultrasound image processing apparatus of claim 1 and an ultrasound probe for providing the ultrasound image processing apparatus with the temporal sequence of ultrasound images of at least a chest region of a fetal entity.

9. A computer-implemented method for visualizing an orientation of the heart of a fetal entity, comprising:
   receiving a temporal sequence of ultrasound images of at least a chest region of a fetal entity from an ultrasound probe, said chest region including the fetal heart, said temporal sequence capturing at least part of a cardiac cycle of the fetal heart;
   identifying the chest region of the fetal entity in one or more of the ultrasound images of said temporal sequence;
   identifying a portion of the spine of said fetal entity in the identified chest region calculating an orientation axis of the fetal chest using the identified chest region and the identified spine portion;
   identifying the septum of the fetal heart as a linear structure which is temporally more stable than its surrounding structures in said temporal sequence of ultrasound images and which defines a region of convergence of movements of the fetal heart during said cardiac cycle;
   calculating an orientation axis of the fetal heart from the identified septum;
   calculating an angle between the orientation axis of the fetal spine and the orientation axis of the fetal heart; and
   generating a control signal for a display device, said control signal causing the display device to visualize at least one of said ultrasound images on a display screen of the display device and generate an overlay over the at least one of said ultrasound images on said display screen, said overlay visualizing the orientation axis of the fetal heart in its calculated orientation, wherein the orientation axis of the fetal heart on the display screen is displayed as a function of the value of the calculated angle between the orientation axis of the fetal chest and the orientation axis of the fetal heart.

10. The computer-implemented method of claim 9, wherein the control signal further causes the display device to visualize the orientation axis of the fetal heart in its calculated orientation within a first sector on the display screen visualizing a defined range of values of said angle if the value of said angle is within said defined range and within a second sector on the display screen if the value of said angle is outside said defined range, preferably wherein the first sector is visualized in a first colour and the second sector is visualized in a second colour different to the first colour.

11. The computer-implemented method of claim 9, wherein the control signal further causes the display device to visualize the orientation axis of the fetal heart in its calculated orientation in a first colour on said display screen if the value of said angle is within a defined range of values for said angle and in a second colour on said display screen if the value of said angle is outside said defined range, optionally wherein the control signal further causes the display device to visualize the orientation axis of the fetal heart in its calculated orientation in a third colour on said display screen if the value of said angle is within a defined distance from an endpoint of said range of values for said angle.

\* \* \* \* \*